United States Patent
Merlau

(10) Patent No.: US 10,733,725 B2
(45) Date of Patent: Aug. 4, 2020

(54) FUNDUS DRAWING ANALYSIS IN OPHTHALMOLOGICAL DIAGNOSTICS

(71) Applicant: Lifesoft, LLC, Winnetka, IL (US)

(72) Inventor: Daniel Joseph Merlau, Winnetka, IL (US)

(73) Assignee: LIFESOFT, LLC, Winnetka, IL (US)

(*) Notice: Subject to any disclaimer, the term of this patent is extended or adjusted under 35 U.S.C. 154(b) by 100 days.

(21) Appl. No.: 15/951,136

(22) Filed: Apr. 11, 2018

(65) Prior Publication Data

US 2019/0318473 A1 Oct. 17, 2019

(51) Int. Cl.
*A61B 3/08* (2006.01)
*A61B 3/14* (2006.01)
*G06T 7/00* (2017.01)
*A61B 3/12* (2006.01)
*G16H 30/40* (2018.01)
*A61B 3/00* (2006.01)
*G16H 50/20* (2018.01)

(52) U.S. Cl.
CPC .............. *G06T 7/0012* (2013.01); *A61B 3/12* (2013.01); *G16H 30/40* (2018.01); *A61B 3/0058* (2013.01); *G06T 2207/30041* (2013.01); *G16H 50/20* (2018.01)

(58) Field of Classification Search
CPC .. A61B 3/102; A61B 3/12; A61B 3/14; A61B 3/0025; A61B 3/032; A61B 3/113; A61B 3/1225; A61B 3/152; A61B 3/10; A61B 3/0083; A61B 3/1005; A61B 3/1025; A61B 3/117; A61B 3/1233; A61B 3/13; A61B 3/132; A61B 3/135; A61B 3/156; A61B 3/185; A61B 5/14555; A61B 90/20; A61B 3/0058; A61B 3/063; A61B 5/1075
USPC ........ 351/200, 205–206, 209–211, 221–223, 351/246
See application file for complete search history.

(56) References Cited

U.S. PATENT DOCUMENTS 7,793,217 B1   9/2010 Kim et al.
2010/0290004 A1* 11/2010 Huang ................. A61B 3/1225
                                                                  351/205

* cited by examiner

*Primary Examiner* — Brandi N Thomas
(74) *Attorney, Agent, or Firm* — Steven M. Greenberg, Esq.; Shutts & Bowen LLP

(57) ABSTRACT

Embodiments of the present invention provide a method, system and computer program product for fundus drawing analysis in ophthalmological diagnostics. A fundus drawing analysis for ophthalmological diagnostics method includes first specifying a set of ophthalmological pathological features of an eye and then generating a database query with the specified set. Thereafter, the database query may be submitted to a database of ophthalmological meta-data regarding different fundus images generated for different eyes so as to retrieve a sub-set of the ophthalmological meta-data. Then, those of the different fundus images that correspond to the sub-set are identified and the identified different fundus images are retrieved. Finally, the retrieved fundus images are displayed in a user interface of a medical image processing host computing system along with a statistical indication of a number of each of the ophthalmological pathological features present in the retrieved fundus images.

5 Claims, 2 Drawing Sheets

FUNDUS DRAWING ANALYSIS IN OPHTHALMOLOGICAL DIAGNOSTICS

BACKGROUND OF THE INVENTION

Field of the Invention

The present invention pertains to the technical field of ophthalmological image processing in the diagnosis of diseases of the eye.

Description of the Related Art

Ophthalmology is a branch of medical science dealing with the structure, functions, and diseases of the eye. An ophthalmologist is a doctor specializing in ophthalmology. Historically, part and parcel of the practice of ophthalmology included the drawing of fundus diagrams. A fundus diagram essentially is a retinal diagram which finds its use in documenting the pathology of the fundus and therefore, provides a basis to detect changes in the fundus at a later time. fundus drawings are drawn in fundus chart. In a fundus chart, generally there are three concentric circles—the innermost circle represents the areas of posterior to the equator, the middle circle represents the area in between equator and ora serrata, and the outermost circle represents the area anterior to the ora serrata.

In drawing a fundus diagram, the ophthalmologist draws the ophthalmologic observation of the retina in proper areas corresponding to the fundus upon a templated drawing of the three concentric circles with radial lines extending from a vertex of the circles. The ophthalmologist draws utilizing different colored pencils to correspond to different observations of the retina and the ophthalmologist annotates the diagram with different universally accepted symbols to express certain observations, such as foreign bodies, sutures, contact lenses, oedmeas, membrane folds, blood vessels, scarring, keratic precipitates, congestions, nodules and pigments, to name a few examples. As well, a lattice between ora serrata and equator is drawn in between the innermost and middle circles. Even further, the optic nerve head is drawn as a small circle. Finally, the radial lines which extend from a vertex of the circles are numbered in roman numerals so as to designate clock hours helpful in describing the location and extent of lesions.

Once a fundus drawing has been created upon a templated fundus diagram, the fundus drawing is incorporated into the file of the patient for subsequent manual retrieval at a next appointment by the patient or in between appointments when the ophthalmologist must determine a diagnosis of the patient and perhaps decide upon a treatment plan. In doing so, the ophthalmologist must, for each patient, re-acquaint himself with the patient file and generate from scratch a diagnosis. Thus, at best the fundus drawing serves as a note of contemporaneous observation to the physician. Consequently, it should be no surprise that the creation and use of the fundus drawing has waned in favor of fundus imaging using a camera.

BRIEF SUMMARY OF THE INVENTION

Embodiments of the present invention address deficiencies of the art in respect to fundus diagramming and provide a novel and non-obvious method, system and computer program product for fundus drawing analysis in ophthalmological diagnostics. In an embodiment of the invention, a fundus drawing analysis for ophthalmological diagnostics method includes first specifying a set of ophthalmological pathological features of an eye and then generating a database query with the specified set. Thereafter, the database query is submitted to a database of ophthalmological meta-data regarding different fundus images generated for different eyes so as to retrieve a sub-set of the ophthalmological meta-data. Then, those of the different fundus images that correspond to the sub-set are identified and the identified different fundus images are retrieved. Finally, the retrieved fundus images are displayed in a user interface of a medical image processing host computing system along with a statistical indication of a number of each of the ophthalmological pathological features present in the retrieved fundus images.

In one aspect of the embodiment, the specifying includes rendering a blank fundus canvas in the user interface, annotating the blank fundus canvas with one or more glyphs representative of corresponding ones of the ophthalmological pathological features, generating corresponding meta-data indicating the corresponding ones of the ophthalmological pathological features of the one or more glyphs annotating the blank fundus canvas and including in the set the corresponding ones of the ophthalmological pathological features of the generated meta-data. Alternatively, the specifying includes loading from fixed storage of the host computing system, a fundus image previously annotated with one or more glyphs representative of corresponding ones of the ophthalmological pathological features, generating corresponding meta-data indicating the corresponding ones of the ophthalmological pathological features of the one or more glyphs, and including in the set the corresponding ones of the ophthalmological pathological features of the generated meta-data. As yet another alternative, the specifying includes loading from fixed storage of the host computing system, a fundus image previously annotated with one or more glyphs representative of corresponding ones of the ophthalmological pathological features, extracting from the fundus image, associated meta-data indicating the corresponding ones of the ophthalmological pathological features of the one or more glyphs, and including in the set the corresponding ones of the ophthalmological pathological features of the generated meta-data.

In even yet another aspect of the embodiment, the annotating includes selecting a display of a tool palette of different glyphs. Each of the different glyphs is representative of a different one of the ophthalmological pathological features. Then, different ones of the glyphs of the tool palette are dragged and dropped onto different portions of the blank fundus canvas. Finally, in even yet another aspect of the embodiment, the generated meta-data includes an indication of a position of each of the glyphs on the blank fundus canvas.

In another embodiment of the invention, a data processing system is configured for fundus drawing analysis for ophthalmological diagnostics. The system includes a host computing system including at least one computer with memory and at least one processor. The system also includes a medical imaging application executing in the memory of the host computing system providing a user interface enabling a drawing canvas and accepting drawing input onto the canvas. The system yet further includes a database accessible in the host computing system of ophthalmological meta-data regarding different fundus images generated for different eyes. Finally, the system includes a fundus drawing analysis module coupled to the medical imaging application.

The module includes program instructions enabled upon execution in the memory to specify in the user interface a set of ophthalmological pathological features of an eye and to generate a database query with the specified set. The program instructions additionally are enabled to query the database regarding different fundus images generated for different eyes and to retrieve in response to the querying a sub-set of the ophthalmological meta-data. The program instructions yet further are enabled to identify ones of the different fundus images corresponding to the sub-set of the ophthalmological meta-data and to retrieve the identified ones of the different fundus images. Finally, the program instruction are enabled to display the retrieved fundus images in the user interface along with a statistical indication of a number of each of the ophthalmological pathological features present in the retrieved fundus images.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for fundus drawing analysis in ophthalmological diagnostics. In accordance with an embodiment of the invention, a set of ophthalmological pathological features of a subject eye are specified in the user interface of a computing system and a database query is generated with the specified set. The database query is then submitted to a database of ophthalmological meta-data regarding different fundus images generated for other, different eyes. Consequently, a sub-set of the ophthalmological meta-data may be retrieved in response to the query and different fundus images corresponding to the sub-set of the ophthalmological meta-data are identified, retrieved from the database and displayed in the user interface along with a statistical indication of a number of each of the ophthalmological pathological features present in the retrieved fundus images. In this way, an ophthalmologist may determine a relevancy of each of the retrieved images to that of the ophthalmological pathological features of the subject eye so as to locate similar fundus images of eyes to that corresponding to the subject eye.

Figure 1:
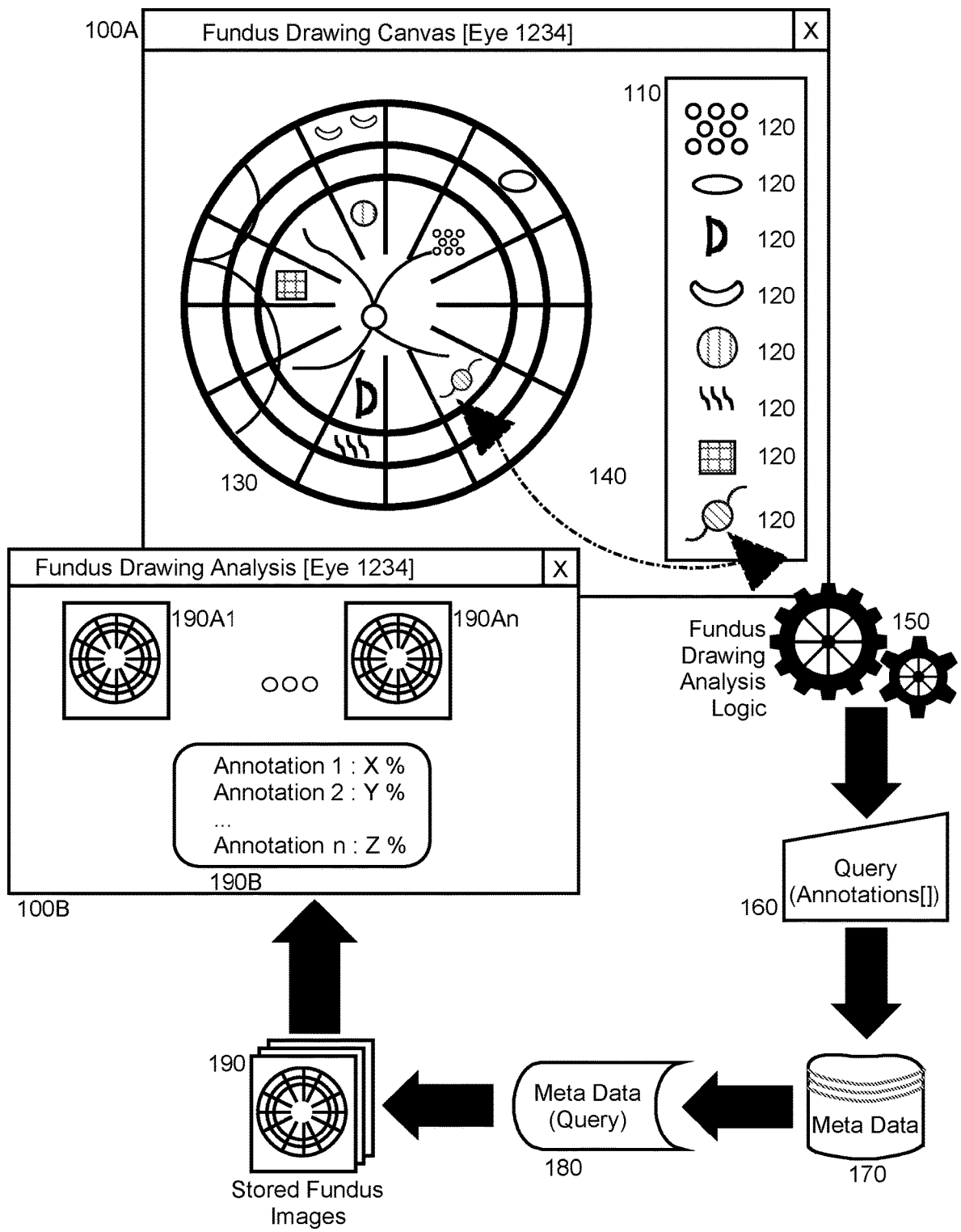
FIG. 1 is pictorial illustration of a process for fundus drawing analysis in ophthalmological diagnostics.

In further illustration, FIG. 1 pictorially shows a process for fundus drawing analysis in ophthalmological diagnostics. As shown in FIG. 1, a Fundus drawing canvas 100A is provided as a user interface into which a Fundus drawing 130 of an eye under observation may be annotated with different Fundus annotations 120 presented in a palette 110 of Fundus annotations 120. In this regard, the Fundus drawing canvas 100A supports a drag-and-drop operation 140 in which one of the Fundus annotations 120 in the palette 110 may be dragged and dropped onto the Fundus drawing 130 so as to indicate a corresponding location in the eye of a corresponding ophthalmological pathological feature observed by the operator of the fundus drawing canvas 100A. Thereafter, the annotated Fundus drawing 130 may be persisted to fixed storage along with corresponding data indicating ones of the annotations 120 present in the Fundus drawing 130 and a location of placement of each of the annotations 120 present in the Fundus drawing 130.

Of note, Fundus drawing analysis logic 150 processes the Fundus drawing 130 so as to identify the ones of the annotations 120 present in the Fundus drawing 130 and the location of placement of each of the annotations 120 present in the Fundus drawing 130. Specifically, the Fundus drawing analysis logic 130 generates a database query 160 incorporating the annotations 120 present in the Fundus drawing 130 against a database of meta-data 170 corresponding to previously stored Fundus images 190. Specifically, the database of meta-data 170 stores therein records correlating different ones of the annotations 120, each with zero or more of the stored Fundus images 190 and optionally, a location of placement of the different ones of the annotations 120 in corresponding ones of the stored Fundus images 190. As such, the query 160 can seek to identify in the database of meta-data 170 records that incorporate one or more of the annotations 120 present in the Fundus drawing 130 and, optionally, one or more of the annotations 120 present in the Fundus drawing also appearing at a similar location in one or more of the stored Fundus images 190.

In response to the query 160, a sub-set of the meta-data 180 is received and associated ones 190A1, 190An of the stored Fundus images 190 are retrieved. As such, the associated ones 190A1, 190An of the stored Fundus images 190 are presented in a user interface 100B. As well, one or more statistics 190B are presented in the user interface 100B. For example, the statistics 190B may indicate a distribution of ones of the annotations 120 present in the associated ones 190A1, 190A2 of the stored Fundus images 190, or the statistics 190B may indicate a distribution of ones of the annotations 120 present in the Fundus drawing 130 that are also present in the associated ones 190A1, 190A2 of the stored Fundus images 190. Consequently, the operator can readily identify a most closely relevant one of the associated ones 190A1, 190A2 of the stored Fundus images 190 so that a previously formulated diagnosis can be retrieved and reviewed in connection with the most closely relevant one of the associated ones 190A1, 190A2 of the stored Fundus images 190.

Figure 2:
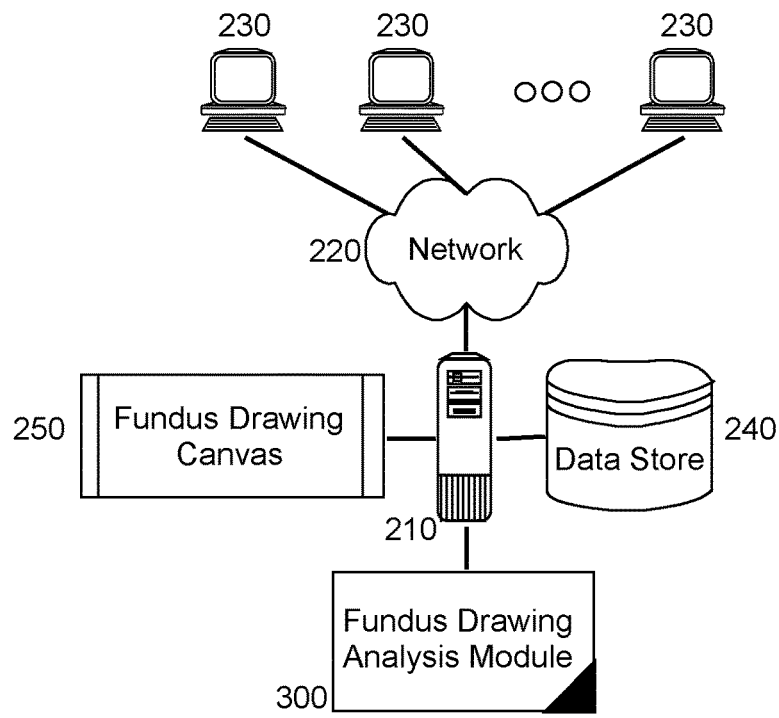
FIG. 2 is a schematic illustration of a data processing system adapted for fundus drawing analysis in ophthalmological diagnostics; and, FIG. 3 is a flow chart illustrating a process for fundus drawing analysis in ophthalmological diagnostics.

The process illustrated in FIG. 1 may be implemented in a data processing system. In yet further illustration, FIG. 2 schematically shows a data processing system adapted for fundus drawing analysis in ophthalmological diagnostics. The system includes a host computing system 210 that may include one or more computers each with memory and at least one processor. The host computing system 210 supports the operation of a Fundus drawing canvas application 250 in which a Fundus drawing may be annotated through the dragging and dropping of different pre-defined annotations onto a blank Fundus canvas. As well, the host computing system 210 is communicatively coupled to different client computers 230 over computer communications network such that the Fundus drawing canvas application 250 may be access by different operators through different ones of the client computers 230 over the computer communications network.

Of import, the system yet further includes a Fundus drawing analysis module 300. The Fundus drawing analysis module 300 includes program instructions that when executed in the memory of the host computing system 210, are enabled to load a selected Fundus image into memory of the host computing system 210 and to extract therefrom, one or more annotations that had been applied to the selected Fundus image. Optionally, one or more corresponding locations of the annotations in the selected Fundus image also may be extracted. As an alternative, a separate file stored in connection with the selected Fundus image may be loaded into memory that includes only data pertaining to the annotations and their respective locations in the selected Fundus image without having loaded for viewing, the selected Fundus image itself.

The program instructions of the Fundus drawing analysis module 300 on execution additionally are enabled to generate a query against meta-data stored in the data store 240 to identify one or more data records storing data correlated to the extracted annotations. In this regard, data store 240 may be a database, a data structure in memory, a table or a file system location such as a folder or directory, or simply a flat file. The program instructions yet further are enabled during execution to generate a sub-set of the meta-data to include only those data records storing data correlated to the extracted annotations and to retrieve corresponding previously stored Fundus images from the data store 240. Finally, the program instructions upon execution are enabled to display in the Fundus drawing canvas application 250, the retrieved, previously stored Fundus images. As well, one or more statistics are computed from the retrieved, previously stored Fundus images such as a frequency of appearance of each of the extracted annotations in the retrieved, previously stored Fundus images and the statistics also are presented in the Fundus drawing canvas application 250.

Figure 3:
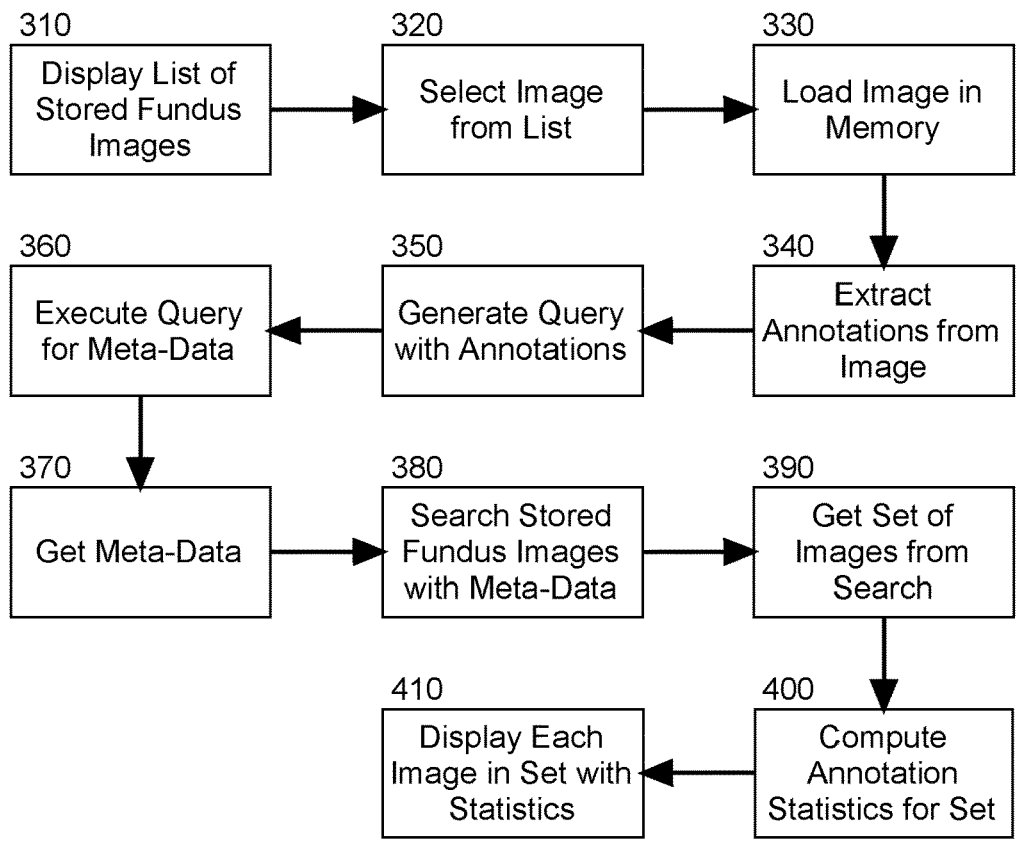

In even yet further illustration of the operation of the Fundus drawing analysis module 300, FIG. 3 is a flow chart illustrating a process for fundus drawing analysis in ophthalmological diagnostics. Beginning in block 310, a list of previously stored Fundus images are retrieved in memory and presented in a display of a user interface to the Fundus drawing canvas application. In block 320, one of the images is selected from the list and in block 330, the image is loaded into memory. In block 340, one or more annotations are extracted from the image and in block 350, a database query is generated utilizing the extracted annotations and in block 360 the database query is executed against a database of meta-data pertaining to the stored Fundus images.

In block 370, meta-data produced by the executed query are received and in block 380, one or more of the stored Fundus images corresponding to the received meta-data are identified. In block 390, the identified Fundus images are retrieved and in block 400, statistics are computed for the retrieved Fundus images. Finally, in block 410, each of the retrieved Fundus images are displayed in a user interface of the Fundus drawing canvas application along with the computed statistics.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:

1. A computer program product for fundus drawing analysis for ophthalmological diagnostics, the computer program product including a computer readable storage medium having program instructions embodied therewith, the program instructions executable by a device to cause the device to perform a method including:

specifying in a user interface of a medical image processing host computing system comprising memory and at least one processor, a set of ophthalmological pathological features of an eye by rendering a blank fundus canvas in the user interface, annotating the blank fundus canvas with one or more glyphs representative of corresponding ones of the ophthalmological pathological features, generating corresponding meta-data indicating the corresponding ones of the ophthalmological pathological features of the one or more glyphs annotating the blank fundus canvas and including in the set the corresponding ones of the ophthalmological pathological features of the generated meta-data;

generating a database query with the specified set;

submitting the database query to a database of ophthalmological meta-data regarding different fundus images generated for different eyes;

retrieving in response to the querying a sub-set of the ophthalmological meta-data;

identifying ones of the different fundus images corresponding to the sub-set of the ophthalmological meta-data;

retrieving the identified ones of the different fundus images; and, displaying the retrieved fundus images in the user interface of the medical image processing host computing system along with a statistical indication of a number of each of the ophthalmological pathological features present in the retrieved fundus images.

2. The computer program product of claim 1, wherein the specifying comprises:

instead of rendering a blank fundus canvas in the user interface, annotating the blank fundus canvas with one or more glyphs representative of corresponding ones of the ophthalmological pathological features, loading from fixed storage of the host computing system, a fundus image previously annotated with one or more glyphs representative of corresponding ones of the ophthalmological pathological features;

generating corresponding meta-data indicating the corresponding ones of the ophthalmological pathological features of the one or more glyphs; and, including in the set the corresponding ones of the ophthalmological pathological features of the generated meta-data.

3. The computer program product of claim 1, wherein the specifying comprises:

instead of rendering a blank fundus canvas in the user interface, annotating the blank fundus canvas with one or more glyphs representative of corresponding ones of the ophthalmological pathological features, loading from fixed storage of the host computing system, a fundus image previously annotated with one or more glyphs representative of corresponding ones of the ophthalmological pathological features;

extracting from the fundus image, associated meta-data indicating the corresponding ones of the ophthalmological pathological features of the one or more glyphs; and, including in the set the corresponding ones of the ophthalmological pathological features of the generated meta-data.

4. The computer program product of claim 1, wherein that annotating comprises:

selecting a display of a tool palette of different glyphs, each representative of a different one of the ophthalmological pathological features; and, dragging and dropping onto different portions of the blank fundus canvas, different ones of the glyphs of the tool palette.

5. The computer program product of claim 1, wherein the generated meta-data includes an indication of a position of each of the glyphs on the blank fundus canvas.

* * * * *